United States Patent [19]

Clement et al.

[11] Patent Number: 4,707,489

[45] Date of Patent: Nov. 17, 1987

[54] INSECTICIDAL AND/OR ACARICIDAL, INCLUDING TERMICIDAL COMPOSITIONS BASED ON 2,5-DISUBSTITUTED DERIVATIVES OF PYRROLIDINE AND/OR PYRROLINE-1

[75] Inventors: Jean-Luc Clement; Michèle Lemaire; Catherine Lange, all of Paris; Gérard Lhommet, Champigny S/Marne; Jean-Pierre Celerier, Paris; Jean-Jacques Basselier, Viry Chatillon; Pierre Cassier, Asnieres, all of France

[73] Assignee: Centre National de la Recherche Scientifique (CNRS), Paris, France

[21] Appl. No.: 727,057

[22] Filed: Apr. 25, 1985

[30] Foreign Application Priority Data

May 4, 1984 [FR] France ................. 84 06980

[51] Int. Cl.$^4$ ............................. A01N 43/36
[52] U.S. Cl. .................................... 514/408
[58] Field of Search ......................... 514/408

[56] References Cited

U.S. PATENT DOCUMENTS

| 2,220,980 | 11/1940 | Horst | 514/408 |
| 2,269,272 | 1/1942 | Krefft | 514/408 |
| 3,228,957 | 1/1966 | Fremery | 548/452 |
| 4,075,320 | 2/1978 | Ritter et al. | 514/408 |

OTHER PUBLICATIONS

T. H. Jones et al., *J. Chem. Ecology*, 8, 1, 1982, p. 285.

T. H. Jones et al., *Tetrahedron Letters*, 21, 1980, p. 789.
C. B. Urbani et al., *Envi. Ent.*, 3, 1974, p. 755.
F. W. Howard et al., *J. Georgia Ent. Soc.*, 14, 1979, p. 259.
F. J. Ritter et al., *Neth. J. Zool.*, 25, 1975, p. 261.

*Primary Examiner*—Albert T. Meyers
*Assistant Examiner*—John M. Kilcoyne
*Attorney, Agent, or Firm*—Cushman, Darby & Cushman

[57] ABSTRACT

Insecticidal and/or acaricidal composition and process for destroying insects, including termites. In an appropriate vehicle, the composition contains as its active substance one or more compounds corresponding to the following general formula:

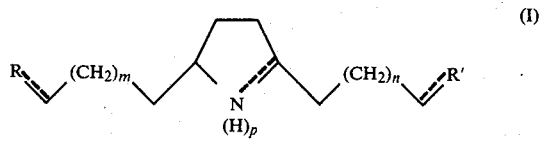

in which:
R and R', which may be identical or different, represent a methyl or methylene radical,
m and n, which may identical or different, stand for 0 or a whole number from 1 to 12, and
p=0 when the heterocycle is pyrroline-1, or p=1 when the heterocycle is pyrrolidine; and the isomers and salts of said compounds of formula (I).

7 Claims, No Drawings

INSECTICIDAL AND/OR ACARICIDAL, INCLUDING TERMICIDAL COMPOSITIONS BASED ON 2,5-DISUBSTITUTED DERIVATIVES OF PYRROLIDINE AND/OR PYRROLINE-1

The present invention concerns new insecticidal and-/or acaricidal, including termicidal, compositions containing 2,5-disubstituted derivatives of pyrrolidine and-/or pyrroline-1 as their active ingredient.

Termites of the genus Reticulitermes, and other insects such as bugs (*Piesma quadrate* or *Cimex lectularium*), crickets (*Locusta migratoria, Gryllus domesticus*), the Diptera, and the Acarina are particularly harmful.

Various insecticidal substances have been proposed to fight these insects, including DTT and related products, organochlorine or phosphorus compounds, methylcarbamates, and pyrethrinoids such as deltamethrine. The last product has proved to be a powerful insecticide at very low doses.

To date, it has not been possible to fight effectively and selectively against termites, which, as is well known, cause varied damage to wooden structures and objects, particularly in certain regions where these insects thrive.

It has now been observed that it is possible to fight very effectively not only against the Isoptera (termites) but also against other insects belonging to the groups Orthoptera (crickets), Heteroptera (bugs), and Diptera, as well as the Acarina, using as an active substance 2,5-disubstituted derivatives of pyrrolidine and/or pyrroline-1, particularly 2,5-dialkyl and 2,5-dialkenyl derivatives.

Some of these derivatives of pyrrolidine and pyrroline-1 have already been described in the literature as components of the poison glands of certain species of ants of the genus Monomorium. To date, they have been considered solely as repellants for use against competitors or as components of the tracking pheromone.

In this regard, the following publications can be cited:
1. T. H. Johnes et al., *J. Chem. Ecology*, 8, 1, 1982, p. 285
2. C. B. Urbani et al., *Envir. Ent.*, 3, 1974, p. 755
3. F. W. Howard et al., *J. Georgia Ent. Soc*, 14, 1979, p. 259
4. F. J. Riter et al., *Neth. J. Zool*, 25, 1975, p. 261
5. T. H. Johnes et al., *Tetrahedron. Lett.*, 21, 1980, p. 789.

The present invention rests on the surprising discovery that these 2,5-disubstituted derivatives of pyrrolidine and pyrroline-1, as well as other related derivatives, possess excellent insecticidal power againat a great variety of insects—including termites of the genus Reticulitermes—and exert powerful acaricidal action.

The present invention therefore relates to a new industrial product consisting of an insecticidal and/or acaricidal, including termicidal, composition containing as its active substance, in an appropriate vehicle, one or more compounds corresponding to the following general formula:

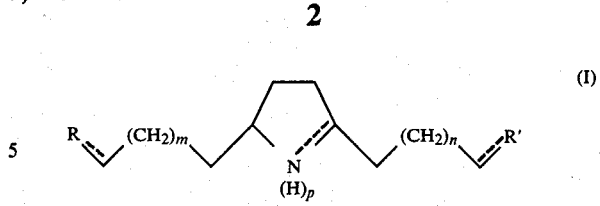

in which:

R and R', which may be identical or different, represent a methyl or methylene radical, m and n, which may be identical or different, stand for 0 or a whole number from 1 to 12, with m+n preferentially being greater than or equal to 4, and p=0 when the heterocycle is pyrroline-1, or p=1 when the heterocycle is pyrrolidine; and the isomers and salts of said compounds of formula (I).

In a first embodiment, the active compounds of the composition are 2,5-disubstituted derivatives of pyrrolidine and correspond to the following formula:

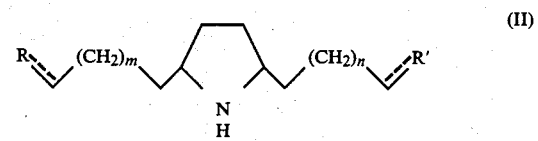

in which: R, R', m, and n have the same meaning as above.

Among the compounds that correspond to formula (II), the following may be cited:
(Hexene-5 yl)-2 (nonene-8 yl)-5 pyrrolidine,
Di(nonene-8 yl)-2,5 pyrrolidine,
Di(decene-9 yl)-2,5 pyrrolidine,
(Hexene-5 yl)-2 nonyl-5 pyrrolidine,
Hexyl-2-nonyl-5 pyrrolidine,
Hexyl-2-pentyl-5 pyrrolidine,
Di hexyl-2,5 pyrrolidine, and
(Hexene-5 yl)-2 pentyl-5 pyrrolidine.

In a second embodiment, the active compounds of the composition are 2,5 disubstituted derivatives of pyrroline-1 and correspond to the following formula:

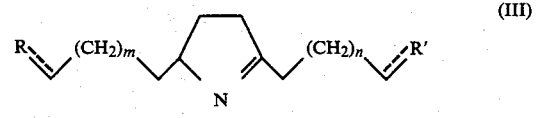

in which: R, R', m, and n have the same meanings as above.

Among the compounds corresponding to formula (III), the following may be cited:
Dihyrdo-3,4(hexene-5 yl)-2(nonene-8 yl)-5, 2H pyrrole, or
Dihydro-3,4 (hexene-5 yl)-2 nonyl-5, 2 H pyrrole.

Tests performed made it possible to show that the stereochemical structure of the active compounds had no appreciable influence on their insecticidal and/or acaricidal activity.

The reasons for this particularly powerful activity have not yet been demonstrated with certainty, but it is supposed that the substances act on the nervous system, with the action being instantaneous and sudden (Knock Down).

After spraying, the insects remain immobilized and die within twelve hours. Given their structure, it is supposed that these active substances possess good liposolubility, which enables them to pass easily through the cuticle of the insects.

Toxicity tests on vertebrates have shown that these substances are not toxic. The lethal dose by subcutaneous injection into mice is greater than 100 mg/kg.

Among the particularly active substances of formula (I) above, the following should be mentioned:
(Hexene-5 yl)-2 (nonene-8 yl)-5 pyrrolidine (compound A)
(Hexene-5 yl)-2 nonyl-5 pyrrolidine (compound B).

Tests performed on various types of European termites of genus Reticulitermes using these two compounds yielded the following results expressed in μg of active substance per mg of termites.

| Lethal dose 50 | Reticulitermes santonensis | Reticulitermes grassei | Reticulitermes banyulensis |
|---|---|---|---|
| Compound A | 0.14 μg | 0.25 μg | 0.18 μg |
| Compound B | 1.30 μg | 2.54 μg | 1.99 μg |

As stated above, some of the compounds of formula (I), and the method by which they are synthesized, have already been described.

To synthesize compounds of formula (II), various methods may be used, including those based on the Hofman-Loffler reaction (D. J. Pedder et al., *Tetrahedron*, 32, 2275 (1976), the reduction to borohydride of the corresponding pyrrolines formed by Mundy's rearrangement (F. J. Ritter et al., U.S. Pat. No. 4,075,320), direct alkylation of N-nitrosopyrrolidine (R. R. Fraser et al., *Synthesis*, 540, 1976), catalytic hydrogenation of pyrroles (T. H. Johnes et al., *Tetrahedron Letters*, 1031, 1979), and reductive amination of diketones-1,4.

The last method has been described by T. H. Johnes et al., *Tetrahedron Letters*, 789 (1980) and is particularly advantageous. It was used to prepare the active substances of the compositions of the invention.

The steps of this method may be represented using the following reaction diagram:

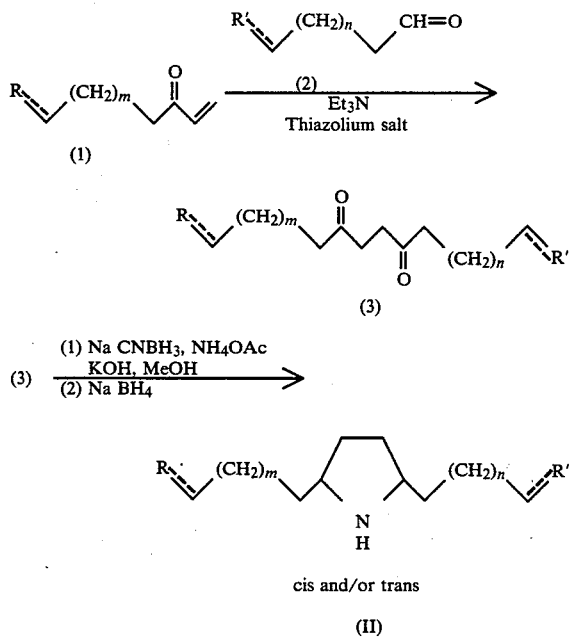

cis and/or trans (II)

According to this method, condensation is used to cause an unsaturated ketone (1) to react with an aldehyde (2) in the catalyzing presence of a thiazolium salt such as the chloride of 5-(2'-hydoxyethyl)-4-methyl-3-benzylthiazolium and in the presence of triethylamine. The condensation reaction is performed with reflux under nitrogen and the diketone obtained (3) is isolated by vacuum distillation and/or by recrystallization in an appropriate solvent.

The 2,5 pyrrolidines of formula (II) are obtained by a reductive amination reaction on the diketones (3) in the presence of ammonium acetate, potash, and sodium cyanoborohydride in methanol for approximately 10 to 24 hours. After the reaction, the mixture is shaken for 2 to 3 hours with a slight excess of sodium borohydride. Then, using conventional methods, the 2,5-pyrrolidines of formula (II) are isolated with a yield of between 50 and 90%.

The pyrrolidine derivatives are most often present in the form of a colorless liquid containing a mixture of cis and trans isomers.

In the course of the reductive amination reaction, pyrroles may form from certain ketones (3), but in quantities that are generally lower than 15%.

The 2,5-disubstituted derivatives of pyrroline-1 df formula (III) are generally obtained from corresponding pyrrolidines by a process using a methanol solution containing an excess of 5% sodium hypochlorite solution.

After reflux for 3 to 5 hours with an excess of about 10 times the necessary quantity of sodium hydroxide, the pyrrolines of formula (III) are obtained in the form of a mixture of isomers.

Although reference was made in formula (III) to a particular isomer, it follows naturally that when the radicals R and R' are different, the pyrrolines may be present in two isomeric forms depending on whether the heterocyclic double bond is in position 2 or position 5.

The unsaturated ketones (1) are generally unstable. They are obtained in two steps according to the following reaction diagram:

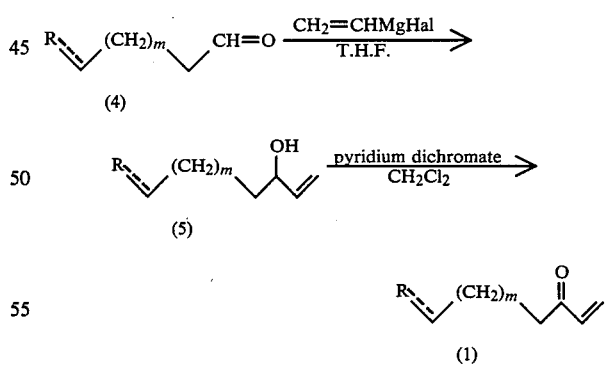

The first step consists of causing magnesium vinyl chloride or bromide to react in THF over a saturated or unsaturated aldehyde of formula (4) and then oxidizing the secondary allyl alcohol in methylene chloride in the presence of pyridium dichromate according to the methods described by F. Bohlmann et al., *Chem. Ber.*, 98, 3010 (1965) and E. J. Corey et al., *Tetrahedron Lett.*, 2647 (1975).

Most of the unsaturated ketones (1) are unstable and must be used as quickly as possible after being prepared.

GENERAL METHOD OF PREPARING THE ACTIVE COMPOUNDS (A) Preparation of the diketones of formula (3)

0.1 mole of ethylene ketone of formula (1), 0.1 mole of aldehyde of formula (2), and 3.2 g of 5-(2'-hydroxyethyl)-4-methyl-3-benzylthiazolium chloride are heated in 18 ml of triethylamine with reflux under nitrogen for 20 hours.

After cooling, 50 ml of ether are added. The precipitate is filtered and washed with small portions of ether. The etherized phases are combined and the solvent is evaporated. The diketone (3) obtained is then distilled in a vacuum.

According to this mode of operation, the following δ diketones are obtained:

Nonadecadiene-1,18, dione-7,10
Yield: 85% F: 40° C. (after Kugelrohr distillation)
RMN at 250 MHz (CDCl$_3$) δ in ppm.
5.55–5.85 2H (CH$_2$=CH—); 4.75–5.05 4H (CH$_2$=CH—);
2.60s, 4H (CO—CH$_2$—CH$_2$—CO), 2.25–2.45 m 4H (CH$_2$ CO), 1.90–2.05 m 4H (CH$_2$—CH=CH$_2$) 1.05–1.65 m 14H (CH$_2$- alkyl).

Docosadiene-1,21, dione-10,13
Yield: 50% F ≈48° (after Kugelrohr distillation)
RMN at 250 MHz δ in ppm (CDCl$_3$)
5.70–5.90 m 2H (CH$_2$=CH—); 4.90–5.10 m 4H (CH$_2$=CH);
2.58 s 4H (—COCH$_2$CH$_2$CO—)
2.45 4H t (CO CH$_2$ . . . ); 1.90–2.10 4H (CH$_2$=CH—CH$_2$—);
1.20–1.80 m 20H (—CH$_2$-alkyl)

Tetrocosadiene-1,23, dione-11,14
Yield: 55% F=72° (recrystallization in methanol)
IR(HCBr$_3$) ν in cm$^{-1}$: 3100, 3040, 1710, 1640, 1150
RMN at 60 MHz (CDCl$_3$) δ in ppm:
5.40–6.10 m, 2H (CH$_2$=CH—); 4.70–5.20 m, 4H (CH$_2$=CH—).
2.66 s, 4H (—CO—CH$_2$—CH$_2$—CO—); 2.25–2.60 m, 4H (CH$_2$—CO);
1.85–2.20 m, 4H (CH$_2$—CH=CH$_2$); 0.95–1.75 m, 24H (CH$_2$-alkyl).

Nonadecandedione-7,10
Yield: 50% E$_{0.01}$225° C. (after Kugelrohr distillation)
RMN at 60 MHz (CDCl$_3$) δ in ppm:
2.65 s, 4H (—CO—CH$_2$—CH$_2$—CO); 2.30–2.60 m, 4H (—CH$_2$—CO):
1.0–1.70 m, 22H (CH$_2$ alkyl); 0.70–0.95 m, 6H (—CH$_2$—CH$_2$CH$_3$).

Hexadecanedione-7,10
Yield: 80% E$_{0.01}$~210° C. (after Kugelrohr distillation)
IR (film) ν in cm$^{-1}$: 3020, 1705, 1460, 1140
RMN at 60 MHz (CDCl$_3$) δ in ppm:
2.75 s, 4H (—CO—CH$_2$ CH$_2$—CO—); 2.40–2.70 m, 4H (—CH$_2$—CO);
1.10–1.80 m, 16H (CH$_2$ alkyl); 0.80–1.05 m, 6H (—CH$_2$—CH$_2$—CH$_3$).

The other diketones of formula (3) are obtained using the same method as that described above.

(B) Preparation of the 2,5-pyrrolidines of formula (II)

A solution containing 0.07 mole of diketone of formula (3), 1 g of powdered potash, 5.5 g of ammonium acetate, and 5 g of sodium cyanoborohydride in 150 ml of anhydrous methanol is shaken for 15 hours. Next, 0.1 mole of sodium borohydride is added and again shaken for 1 hour to terminate the reaction. 100 ml of water are added, and the solution is neutralized with a 10% HCl solution. The solution is then saturated using potassium carbonate and extracted with 4 times 100 ml of CH Cl$_3$. The combined organic phases are dried, the solvent is evaporated, and the resulting liquid is distilled with a Kugelrohr.

Using this method, the following active compounds of formula (II) were obtained:

(Hexene-5 yl)-2 (nonene-8 yl)-5 pyrrolidine cis and trans
Yield 90% E$_{0.01}$190°–210° C. (decomposition)
IR (film) in cm$^{-1}$ 3380; 3040; 1640; 1460; 980; 910.
RMN at 60 MHz (CDCl$_3$) δ in ppm.
5.30–6.0 m, 2H (CH$_2$=CH—); 4.70–5.10 m, 4H (CH$_2$=CH—);
2.70–3.20 m, 2H (—CH—NH—CH—); 1.70, 2.40 m, 8H (CH$_2$—CH=CH$_2$ and CH$_2$ from the cycle),
1.9–2.1 m, 1H (N—H) 1.10–1.70 m, 18H (alkyl —CH$_2$—).

Di-(nonene-8 yl)-2,5 pyrrolidine
Yield: 45%
RMN at 60 MHz δ ppm (CDCl$_3$)
5.45–6.0 m, 2H (CH$_2$=CH— ; 4.75–5.20 m, 4H (CH$_2$=CH—);
2.75–3.20 m, 2H (—CH—NH—CH—); 1.70–2.30 m, 8H (CH$_2$=CH—CH$_2$ from the cycle); 1.0–2.70 m, 24H (—CH$_2$ -alkyl).

Di (decene-9 yl)-2,5 pyrrolidine
Yield: 58% F ≈74° C. (recrystallization in ether)
IR (CHBr$_3$) δ in cm$^{-1}$: 3280, 3100, 3040, 1640, 1455, 1150
RMN at 60 MHz (CDCl$_3$) in ppm:
5.30–6.15 m, 2H (CH$_2$=CH—); 4.75–5.25 m, 4H (CH$_2$=CH—);
3.20–3.80 m, 1H (NH); 2.80–3.30 m, 2H (—CH—NH—CH);
1.75–2.30 m, 8H (CH$_2$—CH=CH$_2$ and CH$_2$ from the cycle);
1.05–1.70 m, 24H (CH$_2$ alkyl).

Hexyl-2 nonyl-5 pyrrolidine
Yield: 50% E$_{0.05}$200°–205° C. (after Kugelrohr distillation)
RMN at 60 MHz (CDCl$_3$) δ in ppm:
5.20–5.40 m, 1H (NH); 2.40–2.95 m, 2H (—CH—NH—CH—);
2.20–2.40 m, 4H (CH$_2$ from the cycle); 1.0–1.80 m, 26H (CH$_2$ alkyl);
0.60–0.95 m, 6H (—CH$_2$—CH$_2$—CH$_3$).

Di-hexyl-2,5 pyrrolidine
Yield: 60% F 163°–165° C. (recrystallization in ethanol)
IR (NCBr$_3$) ν in cm$^{-1}$: 3380, 1580, 1460
RMN at 60 MHz (CDCl$_3$) δ in ppm:
3.20–3.60 m, 2H (—CH—NH—CH—); 1.90–2.0 m, 1H (NH);
1.75–2.30 m, 4H (CH$_2$ from the cycle); 1.05–1.70 m, 20H (CH$_2$ alkyl);
0.80–1.10 m, 6H (—CH$_2$—CH$_2$CH$_3$).

The other active compounds of formula (II) were obtained using the same method as that described above.

The insecticidal and/or acaricidal compositions of the invention can be employed in a form that enables them to be applied easily. For example, the active substances may be used in compositions in the form of emulsions, suspensions, solutions, powders, or aerosols.

For the preparation of sprayable solutions, it is possible to use mineral oil fractions distilled between high and medium temperatures, oils of animal or vegetable origin, aliphatic hydrocarbons such as hexane or pentane, aromatic hydrocarbons such as the alkylated naphtalenes, and tetranaphtalene, which may be mixed with xylenes, cyclohexanols, ketones, halogenated hydrocarbons such as tri- and tetrachloroethane, trichloroethylene, or tri- and tetrachlorobenzene. Preferentially, organic solvents with a boiling point greater than 100° C. are used.

Aqueous preparations may also be used, such as emulsions, pastes, and powders that may be moistened with water.

As dispersing agents, nonionic products are used, such as condensation products of aliphatic alcohol, carboxylic acids or amines having a long-chain hydrocarbon radical containing 10 to 20 carbon atoms with ethylene oxide, such as the condensation product of octadecylic with 25 to 30 molecules of ethylene oxide, that of technical oleylamine with 15 molecules of ethylene oxide, or that of dodecylmercaptan with 12 molecules of ethylene oxide.

Among the anionic dispersants that may be used are the sodium salt of the sulfuric ester of dodecylic alcohol, the sodium salt of dodecylbenzenesulfonic acid, the potassium or triethanolamine salt of oleic acid or of abietic acid, or mixtures of these acides, or the sodium salt of a sulfonic acid of petroleum.

As cationic dispersants, it is possible to use quaternary ammonium compounds such as cetyl pyridinium bromide or dioxyethylbenzyl-dodecylammonium chloride.

It would also be possible to use as a vehicle powdering or dusting agents such as talc, kaolin, bentonite, calcium carbonate, or cork dust, wood dust, or other materials of vegetable origin.

The compositions may also take the form of granules.

The compounds of the invention may also contain other substances capable of improving dispersion, adherence, rain-resistance, or penetrating power.

As additives, it is possible to cite the fatty acids, resins, casein, or alginates.

In a preferred embodiment, the compositions take the form of liquid solutions capable of being sprayed with a gas propellant.

Although the concentration of active substance in the compositions of the invention may vary within broad limits, it is generally not greater than about 10% of the total weight of the composition.

Preferentially, these compositions take the form of solutions or suspensions containing approximately 0.1 to 5% by weight of active substance.

INSECTICIDAL EVALUATION TEST

1. *Termites (Reticulitermes santonensis)*

100 termites of genus *Reticulitermes santonensis* were placed in a glass container. From a distance of 50 cm, the equivalent of 10 μg of (Hexene-5 yl)-2 (nonene-8 yl)-5 pyrrolidine is sprayed from a solution of this substance in pentane.

One minute after the solution was sprayed, it was observed that all of the termites were immobilized. The same was true 24 hours after spraying, which demonstrates the powerful instantaneous action of this substance.

2. Crickets 100 crickets were placed in a container. From a distance of about 50 cm the equivalent of 100 μg of (hexene-5 yl)-2 (nonene-8 yl)-5 pyrrolidine is sprayed from a solution of this substance in pentane. Immediately after spraying a contraction of the crickets' digestive tract and instantaneous immobilization were observed.

Given that a cricket is 200 to 800 heavier than a termite, it can be seen that this substance exerts an especially powerful insecticidal action.

Similar tests were performed with bugs. Excellent results were obtained.

The present invention also concerns a process for destroying insects and Acarina. Said process consists of spraying or spreading, over areas where said insects and Acarina live, an effective quantity of a composition containing one or more active compounds of formula (I) as defined above in a vehicle appropriate for such application.

More particularly, the invention concerns a process for destroying termites in wood structures and objects. Said process consists of spraying or injecting into said wood structures and objects, a composition containing one or more active compounds of formula (I) as defined above in a vehicle appropriate for such application.

We claim:

1. A process for destroying insects or acarians comprising applying to areas where insects or acarians are found an amount of an insecticidal or acaricidal composition effective to destroy said insects or acarians, said insecticidal or acaricidal composition containing in a carrier an effective amount of, but not more than 10 percent by weight based on the total weight of said composition, as an active ingredient for destroying said insects or acarians, a compound having the formula

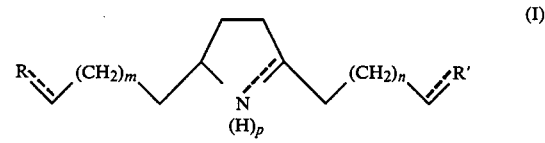

wherein
R and R' each independently represent methyl or methylene,
m and n each independently represent 0 or a whole number ranging from 1 to 12, and
p=0 when the heterocycle is pyrroline-1 or p=1 when the heterocycle is pyrrolidine.

2. The process of claim 1 wherein said compound has the formula

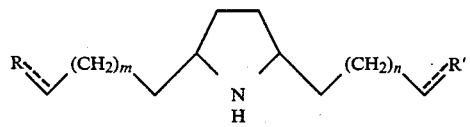

wherein R, R', m and n have the meanings given in claim 1.

3. The process of claim 2 wherein said compound is selected from the group consisting of
(hexene-5 yl)-2 (nonene-8 yl)-5 pyrrolidine,
di (nonene-8 yl)-2,5 pyrrolidine,
di (decene-9 yl)-2,5 pyrrolidine,
(hexene-5 yl)-2 nonyl-5 pyrrolidine,
hexyl-2-nonyl-5 pyrrolidine,
hexyl-2-pentyl-5 pyrrolidine,
di hexyl-2,5 pyrrolidine and
(hexene-5 yl)-2 pentyl-5 pyrrolidine.

4. The process of claim 1 wherein said compound has the formula

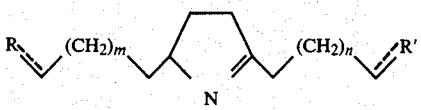

wherein R, R', m and n have the meanings given in claim 1.

5. The process of claim 4 wherein said compound is selected from the group consisting of:
dihydro-3,4 (hexene-5 yl)-2 (nonene-8 yl)-5,2H pyrrole and
dihydro-3,4 (hexene-5 yl)-2 nonyl-5,2H pyrrole.

6. The process of claim 1 wherein said compound is present in an amount ranging from 0.1 to 5 percent by weight based on the total weight of said composition.

7. A process for destroying *Reticulitermes santonensis* and crickets comprising applying to areas where *Reticulitermes santonensis* and crickets are found an amount of a composition, effective to destroy said *Reticulitermes santonensis* and crickets, containing in a carrier an effective amount of, but not more than 10 percent by weight based on the total weight of said composition, as an active ingredient for destroying said *Reticulitermes santonensis* and crickets, a compound having the formula

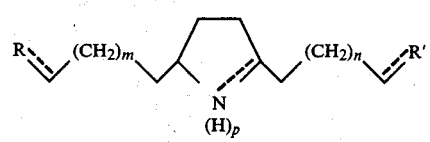

wherein
R and R' each independently represent methyl or methylene.
m and n each independently represent 0 or a whole number ranging from 1 to 12, and
p=0 when the heterocycle is pyrroline-1 or p=1 when the heterocycle is pyrrolidine.

* * * * *